(12) United States Patent
Hansen et al.

(10) Patent No.: US 8,475,420 B2
(45) Date of Patent: Jul. 2, 2013

(54) ARRANGEMENT FOR CONNECTING FECAL RECEIVING BAGS TOGETHER

(75) Inventors: Michael Hansen, Gilleleje (DK); Peter Müllejans, Aalsgaarde (DK)

(73) Assignee: Coloplast A/S, Humlebaek (DK)

( * ) Notice: Subject to any disclaimer, the term of this patent is extended or adjusted under 35 U.S.C. 154(b) by 657 days.

(21) Appl. No.: 12/601,009

(22) PCT Filed: May 20, 2008

(86) PCT No.: PCT/DK2008/050115
§ 371 (c)(1),
(2), (4) Date: May 6, 2010

(87) PCT Pub. No.: WO2008/141652
PCT Pub. Date: Nov. 27, 2008

(65) Prior Publication Data
US 2010/0217214 A1   Aug. 26, 2010

(30) Foreign Application Priority Data

May 21, 2007   (DK) .................................. 2007 00749
Aug. 10, 2007  (DK) .................................. 2007 01138

(51) Int. Cl.
*A61F 5/445* (2006.01)
(52) U.S. Cl.
USPC .......................................... 604/327; 604/332
(58) Field of Classification Search
USPC ........................... 604/327, 332, 333, 335, 349
See application file for complete search history.

(56) References Cited

U.S. PATENT DOCUMENTS

| | | | |
|---|---|---|---|
| 3,825,005 A | 7/1974 | Fenton | |
| 3,841,332 A | 10/1974 | Treacle | |
| 4,387,713 A | 6/1983 | Calanni | |
| 4,784,656 A | 11/1988 | Christian | |
| 4,846,828 A * | 7/1989 | Mendelsohn | 604/387 |
| 5,591,144 A * | 1/1997 | Smith et al. | 604/327 |
| 5,593,389 A * | 1/1997 | Chang | 604/174 |
| 5,643,189 A * | 7/1997 | Masini | 602/58 |
| 5,957,904 A * | 9/1999 | Holland | 604/331 |
| 6,478,763 B1 * | 11/2002 | Simonsen et al. | 602/79 |
| 6,726,667 B2 * | 4/2004 | Leise et al. | 604/339 |
| 6,887,919 B2 * | 5/2005 | Krawinkel et al. | 522/111 |
| 7,513,894 B2 * | 4/2009 | Howlett | 604/355 |
| 2003/0018321 A1 * | 1/2003 | Rosenblum | 604/544 |
| 2003/0191441 A1 * | 10/2003 | Fanti | 604/332 |
| 2006/0106354 A1 * | 5/2006 | Vantroostenberghe | 604/335 |
| 2007/0005033 A1 * | 1/2007 | Ciok et al. | 604/344 |
| 2010/0145291 A1 * | 6/2010 | Kambara | 604/333 |
| 2010/0152686 A1 * | 6/2010 | Ryder et al. | 604/332 |
| 2011/0213322 A1 * | 9/2011 | Cramer et al. | 604/344 |

FOREIGN PATENT DOCUMENTS

| | | |
|---|---|---|
| DE | 4418789 | 11/1995 |
| WO | WO96/19954 | 7/1996 |
| WO | WO99/66859 | 12/1999 |

* cited by examiner

*Primary Examiner* — Susan Su
(74) *Attorney, Agent, or Firm* — Jacobson Holman PLLC

(57) ABSTRACT

An arrangement for connecting fecal receiving bags together provides for a simple coupling arrangement, which provides fluid communication between the bags while preventing odor and fluid to leak from the coupling. Such a coupling arrangement between two receiving devices or bags is discreet and comfortable to wear as the coupling members follow the extent of the receiving devices. The coupling members are furthermore capable of extending parallel to the first and second plane of the receiving devices and thereby reduce the extent to which the coupling members bulge out. A method for connecting fecal receiving bags into a coupling arrangement employs the coupling members.

15 Claims, 9 Drawing Sheets

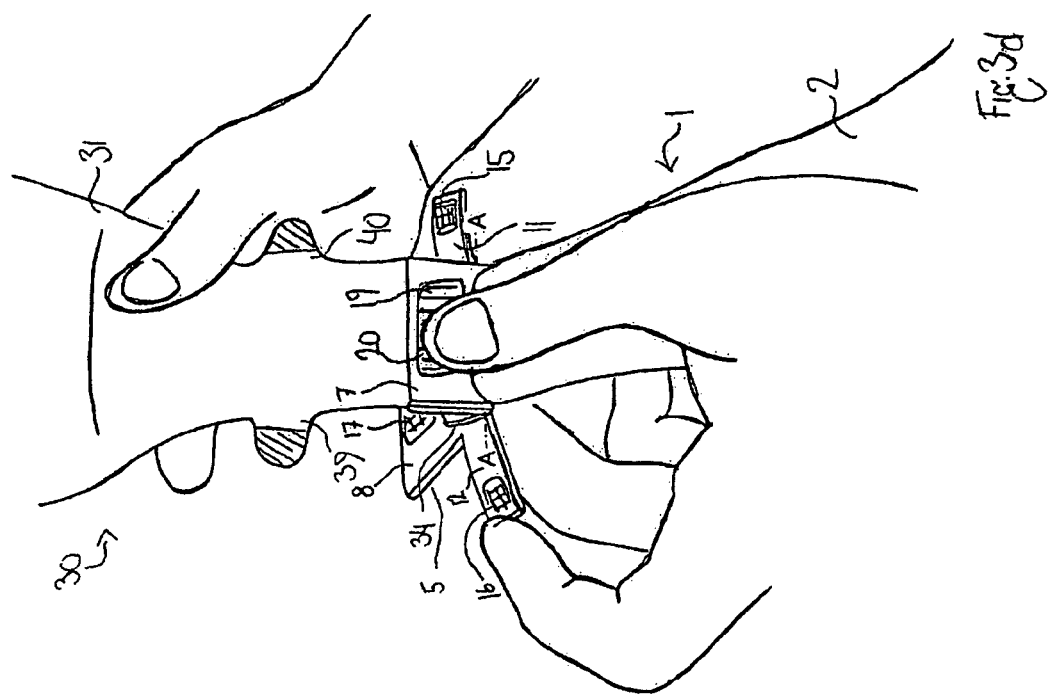
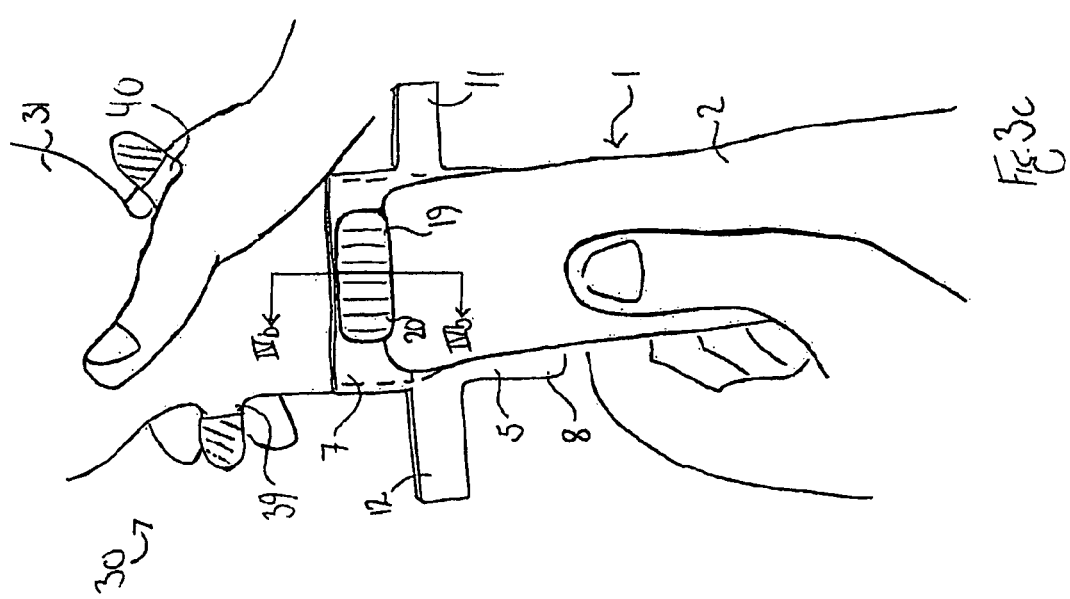

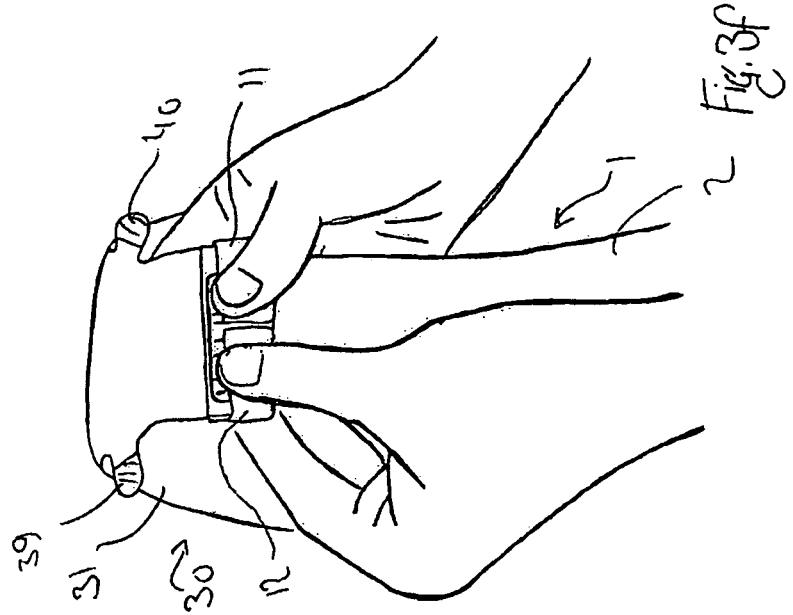
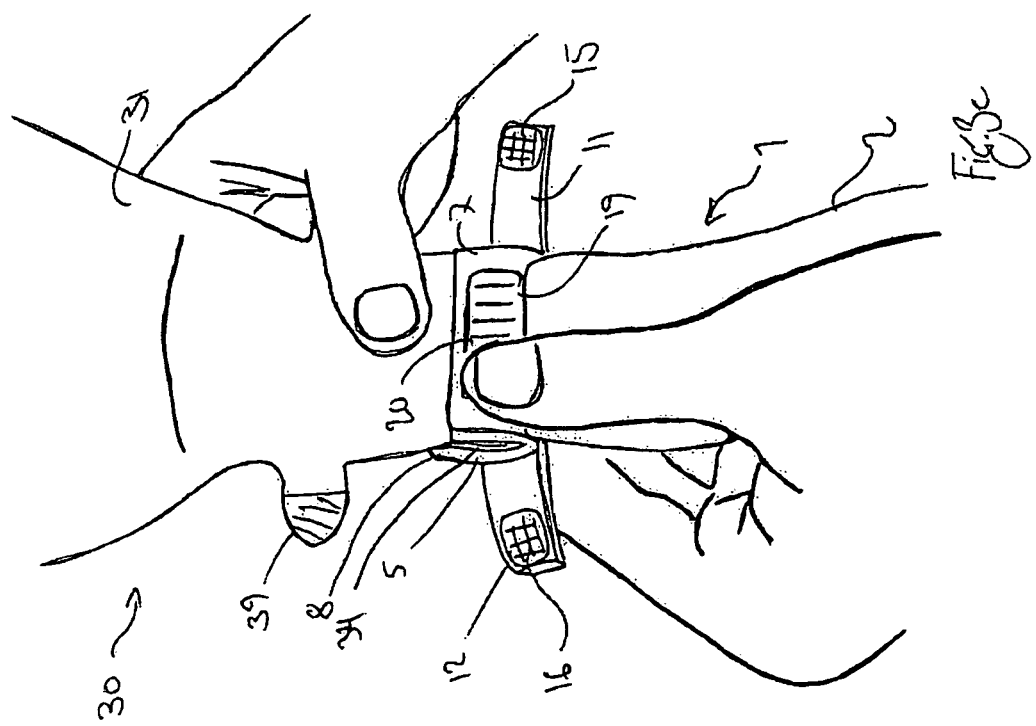

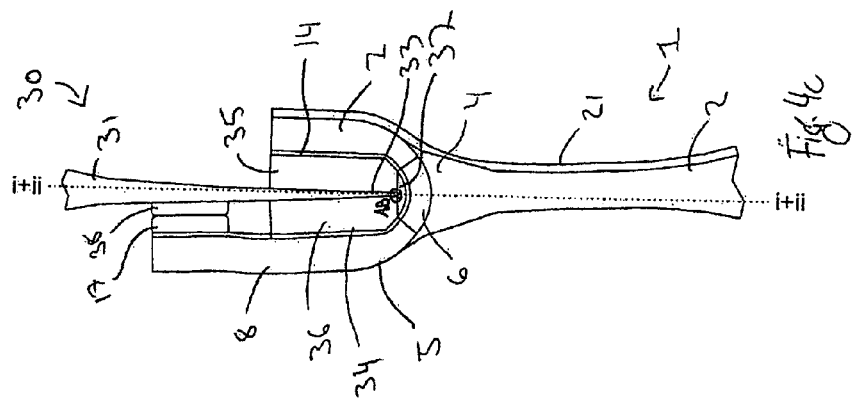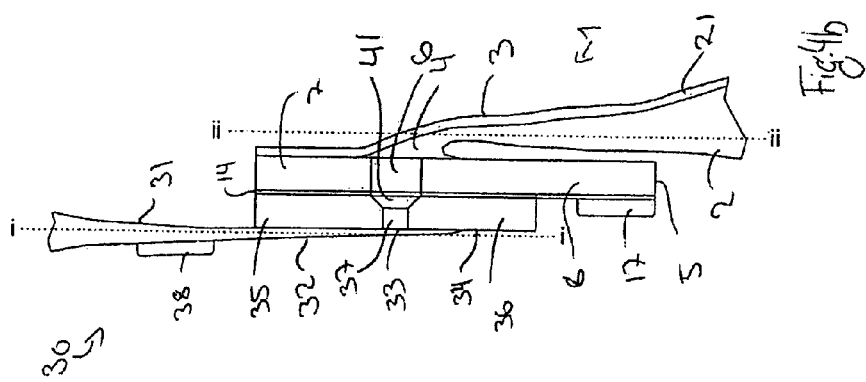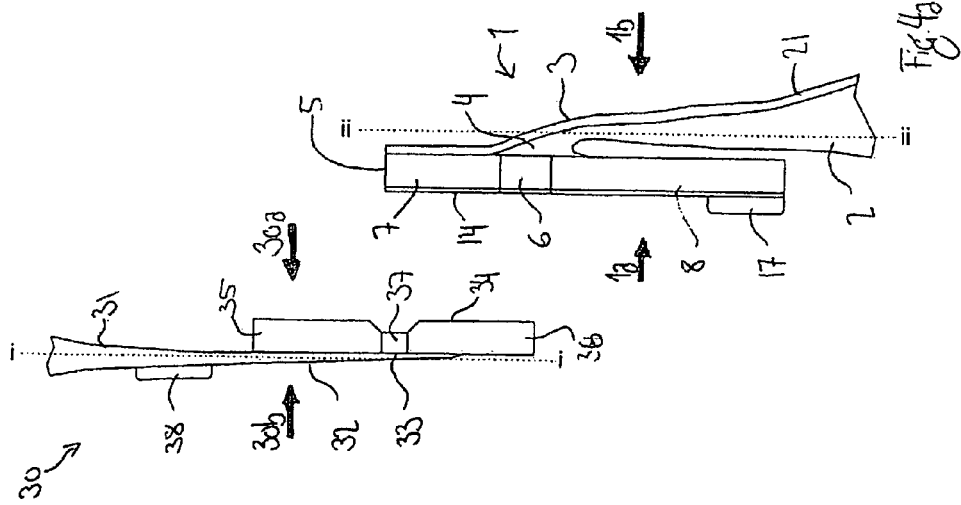

ARRANGEMENT FOR CONNECTING FECAL RECEIVING BAGS TOGETHER

CROSS-REFERENCE TO RELATED APPLICATION

This application is a nationalization of PCT/DK2008/50115 filed May 20, 2008.

BACKGROUND OF THE INVENTION

1. Field of Invention

The present invention relates to an arrangement for connecting fecal receiving bags together in a simple coupling arrangement providing fluid communication between the bags while preventing odor and fluid to leak form the coupling. The invention further relates to a method for connecting fecal receiving bags into a coupling arrangement.

2. Description of the Prior Art

Bedridden persons, for example persons being hospitalized, especially trauma patient who may not be fully conscious often suffer from fecal incontinence. Furthermore, people having an ostomy are often not capable of controlling their discharge. This may understandably result in very unhygienic situations and it is therefore desirable to control the fecal discharges and in particular prevent these discharges from entering the ambient environment, such as a person's bed.

To meet this need ostomy bags have been provided for ostomy users and fecal collecting bags for application around the rectum of anal incontinent persons.

However, it is not always desirable to change the bags every time they are full as this may cause skin irritation. Thus, alternatively it may be desirable to connect an additional collecting bag to the ostomy or fecal collecting bag, which may separately be disconnected when full allowing a new one to be connected.

U.S. Pat. No. 4,784,656 discloses a receptacle for collecting fecal matter from incontinent patients and in particular bedridden incontinent patients.

DE 44 18 798 discloses a lockable container for the medical aid range for the admission of fluids, for example urine or fecal matter.

SUMMARY OF THE INVENTION

In one aspect, the invention relates to a coupling arrangement for fecal management connecting a first fecal receiving device to a second fecal receiving device in a fluid tight manner while allowing flow in a flow direction from the first fecal receiving device to the second fecal receiving device or vice versa; a first opening provided in a first end of a first bag of the first fecal receiving device and a second opening provided in a second end of a second bag of the second fecal receiving device, wherein the coupling arrangement further comprises, that the first end and the second end define a respective first and second plane; a first planar coupling member arranged at least partly around the first opening; a second planar coupling member arranged at least partly around the second opening; that a first proximal surface of the first planar coupling member is placed against a second proximal surface of the second planar coupling member and that the first planar coupling member is attached to the second planar coupling member enabling the first plane and the second plane to be parallel arranged and at least partly aligning the first and second opening.

This provides a coupling arrangement between two receiving devices which is discreet and comfortable to wear as the coupling members follow the extent of the receiving devices as they are capable of extending parallel to the first and second plane of the receiving devices and thereby reduces the extent to which the coupling members bulge out. It can be understood that it will basically be the thickness of the planar coupling members which determines how much the coupling arrangement bulges.

In the following, when referring to a part or element herein as being 'planar' it should be understood that this part mainly extends in one plane and has a relative small thickness compared to the extent of the part in said plane. As an example a piece paper is a planar part extending in one plane defining two dominating sides. In the context herein, it should also be understood that planar should be understood relative to an extruded tubular element, e.g. a hose, having an almost uniform radius.

Furthermore, it should be understood that even though the first and second planes are purely mathematical elements having only two dimensions the first and second ends extend in all three dimensions. However, as understood with relation to the term 'planar' the first and second plane indicates the directions in which the major part of the first and second end extends.

In the present context, when referring to proximal and distal surfaces this should be read when the receiving devices are held in a position where the respective first and second openings face the observer. Thus, a proximal surface is the surface of an element or part that faces the observer when the first or second opening open out towards the observer. Accordingly, the distal surface faces away from the observer when he or she can see the opening.

In one embodiment a coupling arrangement will be disclosed for fecal management wherein the first planar coupling member is formed with a first through going hole communicating with the first opening, said first through going hole defines a first proximal planar part and a first distal planar part of the first planar coupling member, the second planar coupling member is formed with a second through going hole communicating with the second opening, said second through going hole defines a second proximal planar part and a second distal planar part of the second planar coupling member, and the first proximal planar part is placed against the second distal planar part and the first distal planar part is placed against the second proximal planar part.

In the present context, when referring to proximal and distal part and elements this should be read when the receiving devices are held in a position where the respective first distal planar part and second distal planar part are furthest away from the observer relative to the respective first proximal planar part and second proximal planar part. Thus, the first planar coupling member and the second coupling member are closest to the observer while the respective first and second bag extends away from the observer along the first or second plane.

In a second aspect, there is provided a fecal receiving device for use in fecal management comprising a first bag with an opening provided in a first end of the bag and a first planar coupling member having a first through going hole, the first opening is arranged around the first through going hole providing fluid communication from the first bag and out through the first through going hole, wherein the first end defines a respective first plane.

This provides a receiving bag having elements which provides easy coupling with the outlet of other receiving bags, for example ostomy bags or bags for fecal incontinence.

In one embodiment the first through going hole of the fecal receiving device defines a first proximal planar part and a first distal planar part of the first planar coupling member. The first planar coupling member has a longer extent than the first through going hole, whereby the first proximal planar part and the first distal planar part are connected to each other in peripheral areas at the end of the first through going hole. The peripheral areas may furthermore function as hinges, allowing the first planar parts to be folded relatively to each other.

In order to be able to secure the receiving device to other elements, the fecal receiving device may comprise a first locking strip and a second locking strip projecting from the first proximal planar part.

In one embodiment a biasing element is arranged across at least a part of the first bag and a part of the first planar coupling member. The biasing element biases the bag and the coupling member into a predetermined position relative to each other. Thus a controlled orientation of the first planar coupling member relative to the receiving device can be achieved. In one embodiment thereof, said biasing element can be made of a sheet material having a higher resilience than the material of the first bag.

In a third aspect, a method is provided for connecting a first fecal receiving device and a second fecal receiving device into a coupling arrangement as described, comprising the steps of axially aligning the first opening with the second opening; and arranging the first receiving device and the second receiving device in a coupling position where the first planar coupling member is placed against the second planar coupling member.

This provides a method wherein a leak and odor tight coupling arrangement may be easily provided and which provides a sealing arrangement allowing easy flow of fecal matter.

BRIEF DESCRIPTION OF THE DRAWINGS

FIG. 3a-3g illustrate how the first and second fecal receiving device are arranged in a coupling arrangement, FIG. 4a-4c show selected stages of the coupling arrangement above seen in section, and FIG. 5a-5b coupling arrangements when matter is flowing through.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1A:
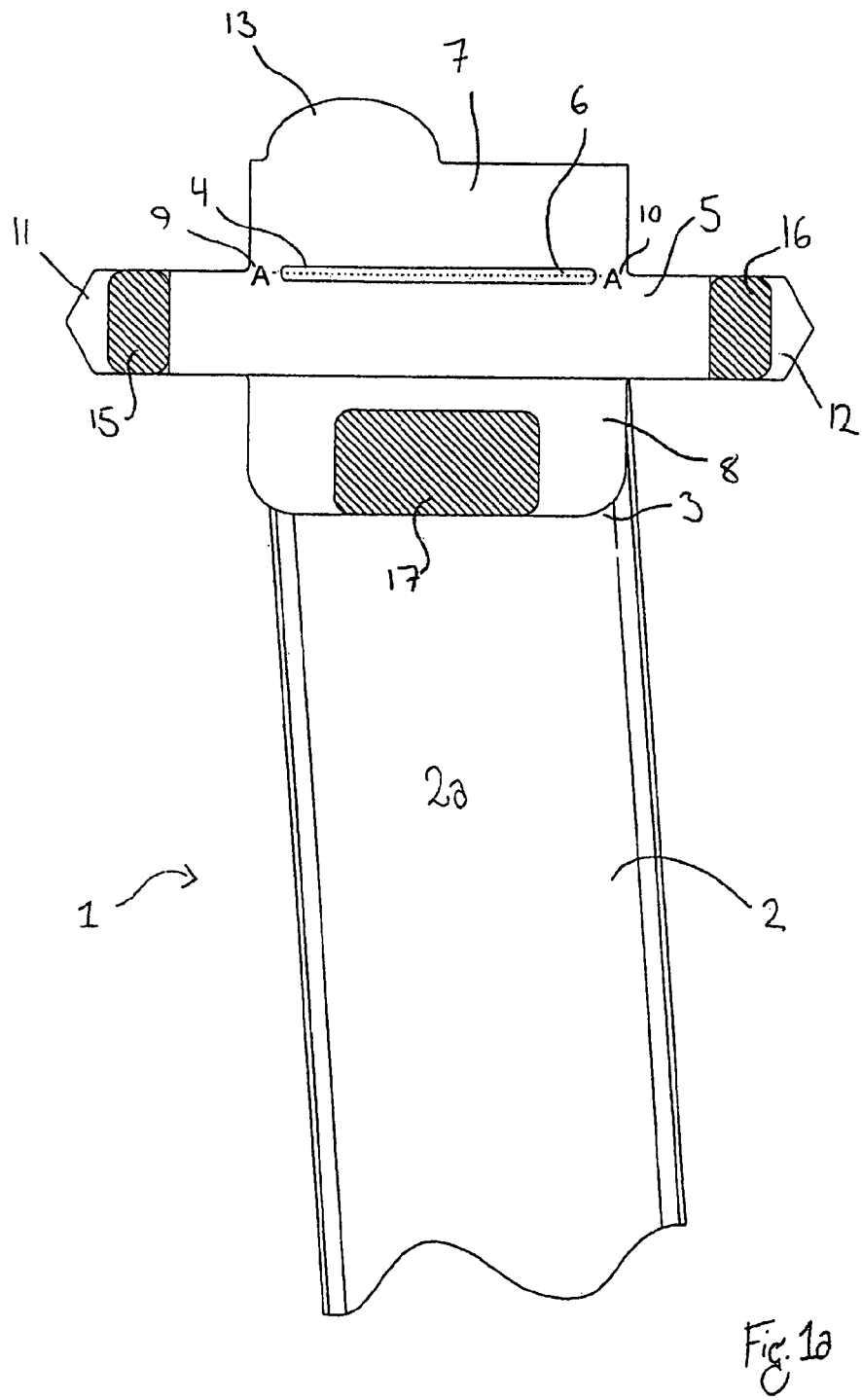
FIGS. 1a and 1b show a first fecal receiving device from a proximal side and a distal side respectively.
Figure 1B:
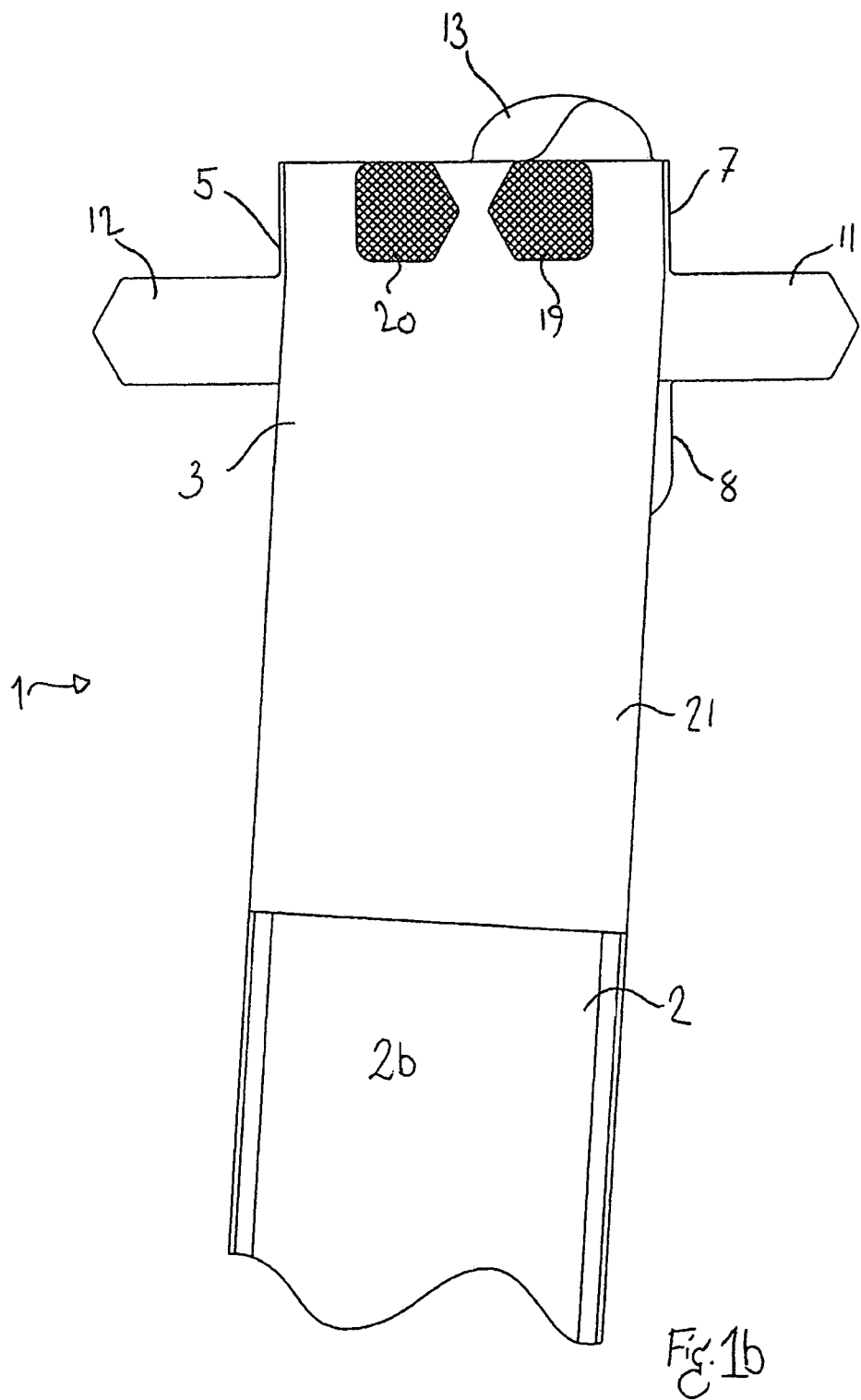

Fig. 1a and 1b show a first fecal receiving device 1 seen from a front side (proximal side) and a rear side (distal side) respectively.

The first fecal receiving device is formed of a first receiving bag 2 defining a first compartment. In a first end 3, the receiving device is open through a first opening 4, defined by a peripheral edge of the first receiving bag 2.

In the following the proximal and distal surfaces of different element and parts will be referred to with the parts reference number followed by the designation 'a' for the proximal side/surface and 'b' for the distal side/surface. Thus, the proximal surface of the first receiving bag will be referred to as 2a.

The first fecal receiving device is further provided with a first planar coupling member 5 in the shape of a plane foam member having a thickness of 1 mm. The foam can for example be made of foam with an adhesive, e.g. a polyethylene/ethylene vinyl acetate (PE/EVA) foam with an acrylic adhesive. A first through going hole 6 extending transverse to the flow direction is provided in the first planar coupling member 5. The first through going hole 6 is in the form of an elongated opening or slit. The first through going hole 6 divides the first planar coupling member in a first proximal planar part 7 on one side of the first through going hole and a first distal planar part 8 on the other side of the first through going hole. In the following, the first proximal planar 7 will also be referred to as the first adhesive part 7 and the first distal planar part will also be referred to as the second adhesive part 8.

The adhesive parts 7, 8 are longer than the elongated opening 6 and as they are provided as a single unit they are joined at both ends of the elongated opening 6, providing a first peripheral area 9 and a second peripheral area 10.

This provides a single first planar coupling member 5 wherein the first adhesive part and the second adhesive part are integrated. Thus, if one part is rotated or tilted the other will follow. However, the first planar coupling member may be formed of a flexible material, having a flexibility which allows the first planar coupling member to be folded manually, providing a bend along the longitudinal axis A-A of the elongated opening 6, i.e. the longitudinal axis A-A corresponds to the folding axis as described previously.

The first planar coupling member 5 and the first receiving bag 2 is attached to each other by welding the peripheral edge of the first opening 4 to the first planar coupling member at the edge, or to an area surrounding the edge of the first elongated opening 6. Thereby providing fluid communication from the first compartment out through the first elongated opening. Alternatively, the first planar coupling member 5 and the first receiving bag 2 may be glued together or otherwise attached. In this assembled configuration, the rear (distal) side 5b of the first planar coupling member is the side on which the first receiving bag is attached and the front (proximal) side 5a is the side on which the compartment opens out through the first through going hole 6.

The rear (distal) side 2b of the first receiving bag 2 is the side of the bag facing the same direction as the rear side of the first planar coupling member in the position seen in FIGS. 1a and 1b. The first receiving bag can be formed as a single tubular body. Alternatively, it can be formed as two sheet layers welded together along the sides. The bag material can be formed of any material impervious to odor and liquid and it may be skin friendly allowing a user to have the first receiving bag to be in contact against his/hers skin for a longer period of time. Such materials may for example be a foil in the form of a laminate made of PVdc and EVA.

The first planar coupling member 5 may be formed of a material that is at least slightly stiffer than the material of the bag. The material of the first planar coupling member may moreover be more resilient than the bag material, which allows the first planar coupling member to return to its original shape when not influenced by outside forces. Alternatively or additionally, the first planar coupling member may also have a flexibility allowing it to be bend manually, i.e. a user should be able to easily fold the wafer using his or her hands. Accordingly, the first planar coupling member material may for example be a foam showing thermoplastic characteristics such as silicone materials, SEBS, conventional rubber materials or combinations and blends thereof or materials having characteristics to thermoplastic materials such as polyurethane foams or polyethylene foams.

A first locking strip 11 and a second locking strip 12 extend from the first distal planar part 8 of the first planar coupling member 5 outwards in a direction parallel to the extent of the longitudinal axis A-A, of the first elongated opening 6. In other words, the first and second locking strips extend transverse to the flow direction from opposite sides of the planar coupling member. As can be seen, one edge of each of the first and second locking strip is flush with the elongated opening, i.e. coincide with the longitudinal axis A-A.

A release liner 13 covers an adhesive layer 14 (disposed between the release liner and the first planar coupling member, see FIGS. 4a-4c) is disposed around the first through going elongated opening 6 on the proximal side of the first adhesive part 7 and at least partly on the proximal side of the second adhesive part 8, the first locking strip 11 and the second locking strip 12.

In alternative embodiments, the adhesive layer can be provided only partly on the first adhesive part and the second adhesive part, e.g. as tracks extending across the two parts parallel to the longitudinal axis A-A of the first slit.

It should be understood that the adhesive might be provided in many different ways. For example, if it is desired to provide a one-time only coupling, then the adhesive can be provided all over the proximal surface of the first planar coupling member. Thus, it provides a secure attachment, which can be difficult to detach without breaking any parts of the coupling assembly. However, if a user should be able to reattach the coupling arrangement then a small part of the proximal surface of the first planar coupling member can have adhesive provided thereon. Such a small part may be an area surrounding the first elongated opening, for example in a radius of a few millimeters, e.g. 3 mm, around the periphery of the opening. Furthermore, different types of adhesives may be used in order to achieve different adhesive properties.

On the proximal side of the first locking strip 11, the second locking strip 12 and the second adhesive part 8 a first 15, a second 16 and a third 17 Velcro® hooks patches are respectively provided. These are provided on parts of the areas, which are not covered by the adhesive layer. On the distal side of the first adhesive part 7, a first and a second Velcro® loop patch 19 and 20 are provided.

By this arrangement, the first planar coupling member 5 is at least partly rotatable around the longitudinal axis A-A of the first elongated opening 6, i.e. the axis transverse to the axis of the first opening and the general direction of the flow of fecal matter though the first receiving device when in a coupled arrangement as will be described below.

The position shown in FIGS. 1a and 1b, where the distal side 8b of the second adhesive part 8 faces the proximal side 2a of the first receiving bag 2 is the position wherein the first receiving device is ready to be arranged in a coupling arrangement as will be described below. In order to bias the first planar coupling member into this position a biasing element 21 may be provided, which extends continuously from the distal side 2b of the first receiving bag 2 to the distal side 7b of the first adhesive part 7. Such a biasing element can simply be a sheet material glued or otherwise attached to the first bag 2 as shown. Alternatively, it can be a number of longitudinal extending ribs or another configuration, which crosses the weld along the distal side of the bag and the first adhesive part.

The biasing element 21 may be formed of a relative thick material compared to the wall material of the first receiving bag and/or the material may have a high resilience compared to the wall material of the first receiving bag.

On the distal side 21b of the biasing element, instructions for use of the first receiving device and how to provide a coupling arrangement are provided. Furthermore, the biasing element may have a surface which matches the texture and feel of the surface of the bag, such as the non-woven layer formed as a comfort layer consisting of e.g. elastic spunbond non-woven made from polyurethane and polyethylene, or polyester (PET) fibers.

The first receiving device is only shown partly in FIGS. 1a and 1b. The first receiving device may continue in an elongated tubular fashion and at an end opposite the first end 3 be connected to a larger collection container or arranged within the bowl of a toilet. Alternatively the first receiving bag may expand into a collection device for collecting fecal matter.

Figure 2:
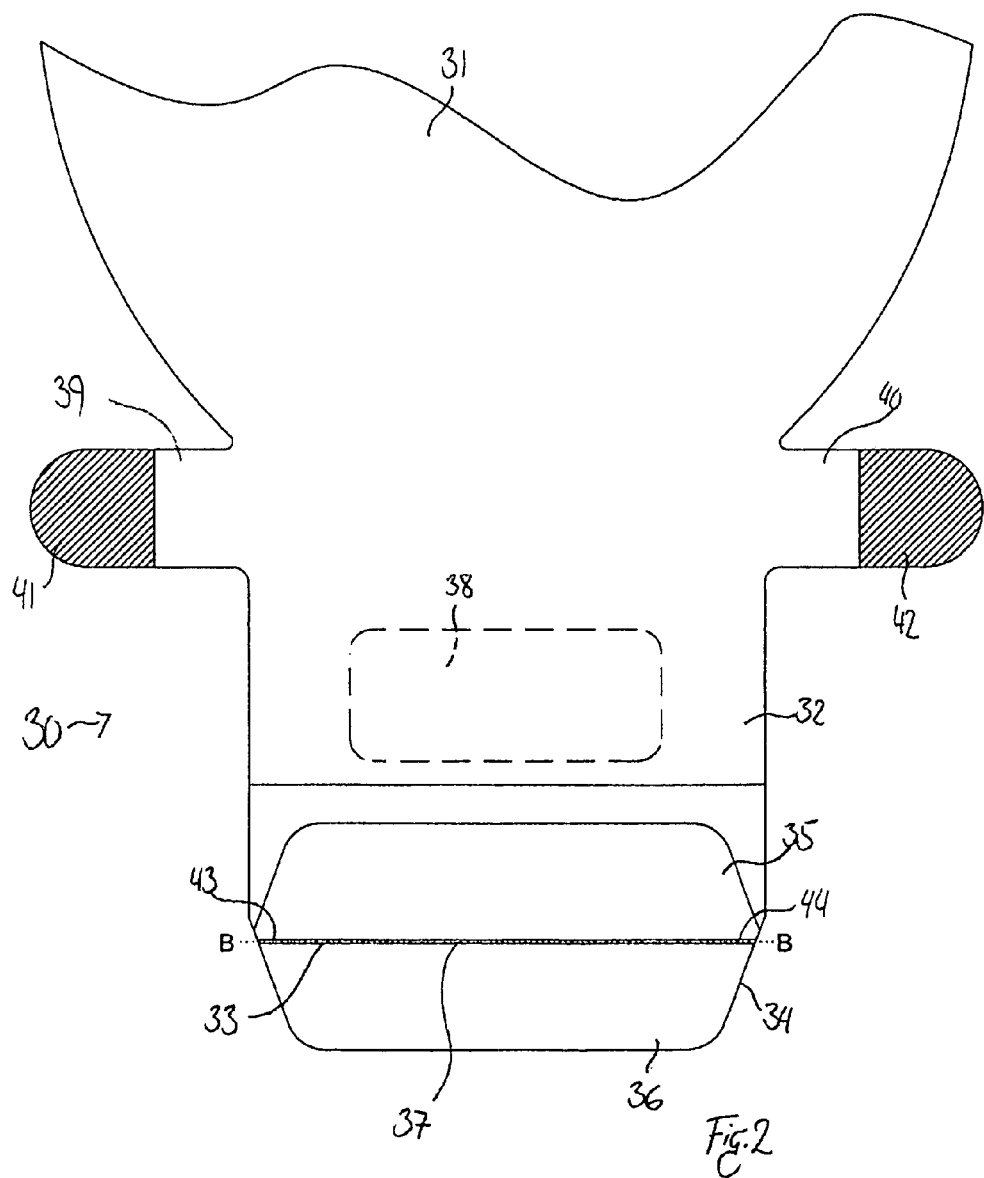
FIG. 2 shows a second fecal receiving device from a proximal side.

FIG. 2 shows a second receiving device 30. The second receiving device 30 comprises a second receiving bag 31 defining a second compartment. At a second end 32 the second receiving bag has a second opening 33.

The second receiving device 30 is adapted in order to be connected to receive fecal matter from the rectum or a stoma of the user. In such embodiment, an adhesive flange (not shown) having a through going hole will typically be arranged around an opening (not shown) of the receiving bag. The adhesive flange will then be capable of adhering to the second receiving device around the rectum or stoma of a user. Such adhesive constructions, in particular ostomy bags, are generally known by the person skilled in the art and will thus not be further described herein.

At the second end 32 the second receiving device is provided with a Hide-away® outlet produced by Coloplast A/S and which is described in WO 99/66859. Hide-away® outlets provides an outlet for discharging the contents from the second receiving bag while being able to be closed into an odor and liquid tight closure which is discreet and comfortable to wear.

In the embodiment shown in FIG. 2 the Hide-away® outlet comprises a second planar coupling member 34 formed of a second distal planar part 35 in the shape of a first sealing plate 35, and a second proximal planar part 36 in the shape of a second sealing plate 36. The sealing plates are arranged on opposite sides of the second opening 33 thereby defining the second opening as a second through going elongated opening 37 extending transverse to the flow direction. The sealing plates may in some embodiments be arranged so close together that the second through going elongated opening basically forms a slit.

In FIG. 2 the second receiving device is shown from the front (proximal) side 30a, which is the side on which the second through going elongated opening is provided. On the rear (distal) side 30b of the second receiving device above the first sealing plate 35, when seen in flow direction when the second opening 33 functions as an outlet opening a second Velcro® loop patch 38 is provided. Above the second Velcro® loop patch, a third locking strip 39 and a fourth locking strip 40 are provided protruding from the side of the second receiving bag in a direction parallel to the longitudinal axis B-B of the second through going opening, i.e., transverse to the flow direction. On the proximal side of the third and fourth ear fourth 41 and fifth 42 Velcro® hook patches are respectively provided. The third and fourth locking strip are used when closing the Hide-away® outlet as can be understood from WO 99/66859 and is thus not used in the coupling arrangement as described below.

The first sealing plate 35 and the second sealing plate 36 are connected to each other via first and second hinge elements 43 and 44.

FIG. 3a-3g illustrates a method for connecting a first fecal receiving device 1 and a second fecal receiving device 30 into a coupling arrangement providing fluid communication between the first and second compartment while also providing an odor and liquid tight seal.

Figure 3B:
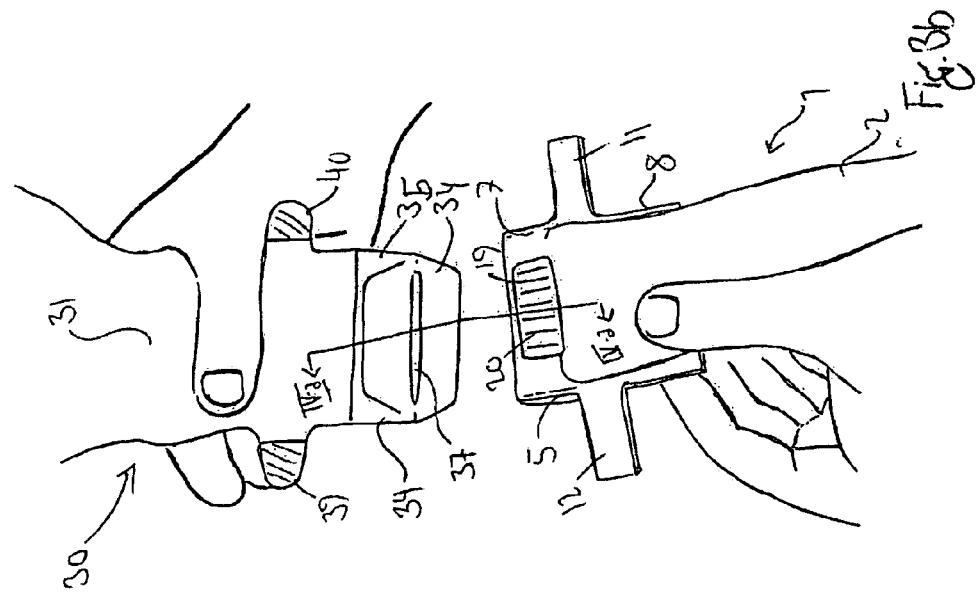
Figure 3A:
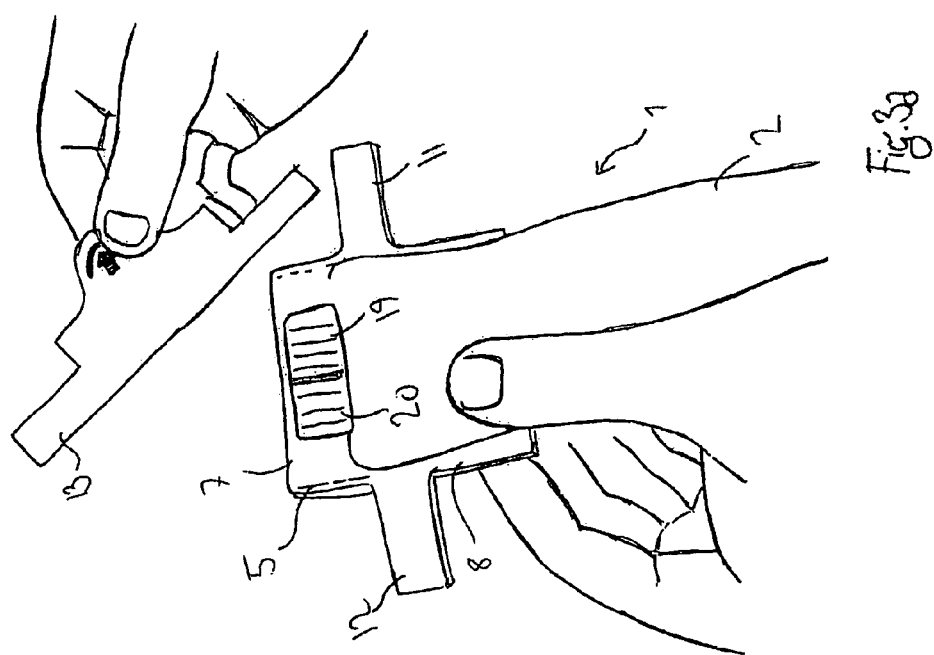

FIG. 3a shows a user handling the first fecal receiving device 1. To prepare the first fecal receiving device for use, the user removes the release liner 13 covering the adhesive layer.

As shown in FIGS. 3b and 3c, the first fecal receiving device 1 and the second fecal receiving device 30 are initially connected by having the proximal side 5a of the first planar coupling member 5 face the proximal side 31a of the second receiving bag 31 and thereby the proximal side of the first and second sealing member 35 and 36. Thus, the first through going elongated opening 6 and the second through going elongated opening 37 face each other.

The first through going elongated opening 6 and the second through going elongated opening 37 are then aligned. By providing an adhesive layer between the first planar coupling member and the second planar coupling member, the receiving devices may be connected to each other by pressing the first planar coupling member 5 against the second planar coupling member 34 so that the first adhesive part 7 and the first sealing plate 35 at least partly adheres together and the second adhesive part 8 and the second sealing plate 36 at least partly adhere together. In some embodiments, a releasable adhesive may be used that allows for the elements to be separated and reattached for e.g. re-alignment or exchanging receiving devices.

As can be seen in FIG. 3d, the second adhesive part 8 is folded around the longitudinal axis A-A of the first through going elongated opening 6. When folded approximately 180° around the longitudinal axis, the third Velcro® hook patch 17 on the first planar coupling member 5 engages with the second Velcro® loop patch 38 arranged on the distal side 31b of the second receiving bag 31. This prevents the folded coupling arrangement from unfolding.

Figure 3E:
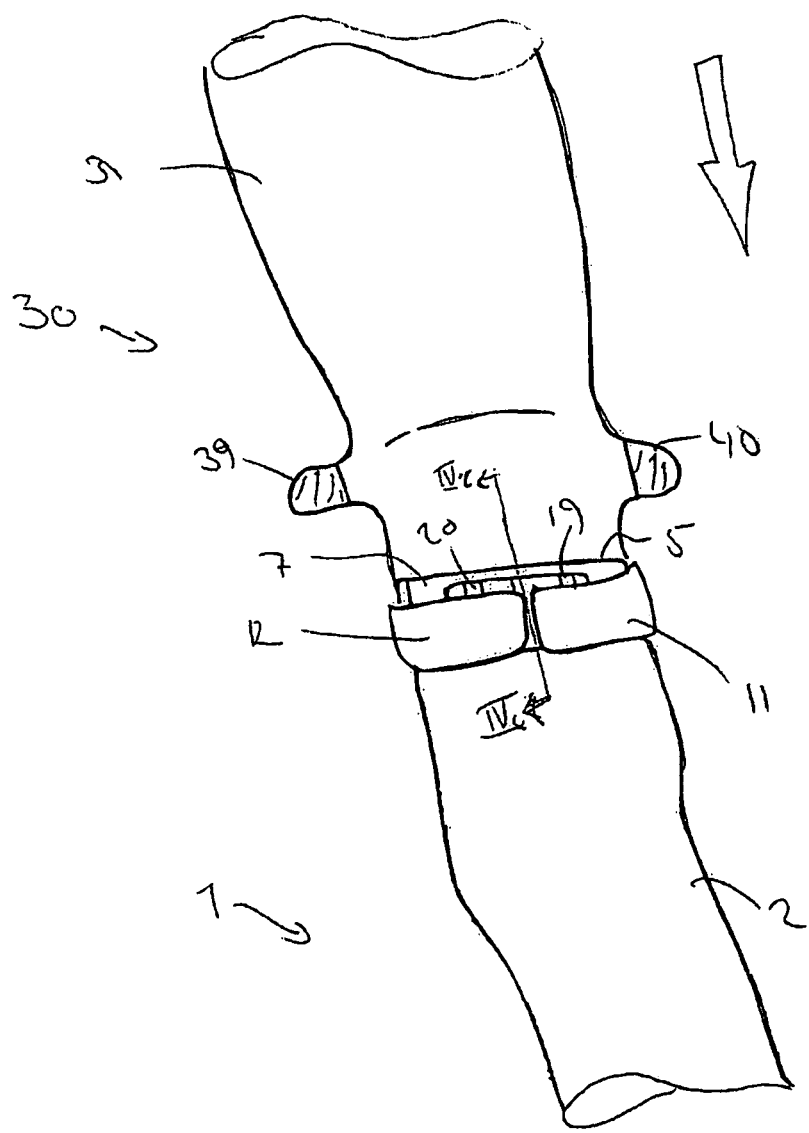

Thus, as seen in FIG. 3e a coupling arrangement is provided which is secured in a coupling position wherein the plane of the first receiving bag and second receiving bag has been aligned.

To further secure the coupling arrangement and to prevent leaks mitigating from the connection between the first and second through going elongated opening 6,37 along the fold along the longitudinal axis A-A of the first through going elongated opening, the first and second locking strip 11,12 are tightly folded around the coupling arrangement so that the first Velcro® hook patch 15 and the second Velcro® hook patch 16 engage with the Velcro® loop patches 19 and 20 as shown in FIG. 3f.

While the locking strips helps in securing the coupling arrangement and reduce the risk of unfolding, they also close possible leaks occurring from channels created in the fold along the longitudinal axis A-A propagating from the first and second openings and outwards. Moreover, the locking strips may be formed of an elastic material allowing it to be stretched providing a tight closure which provides for an odor and liquid tight seal.

Thus, a coupling arrangement is provided as seen in FIG. 3g that provides a secure and odor and leak proof connection between the first fecal receiving device and the second fecal receiving device. As can be understood, the fecal matter from the rectum or the stoma will be collected by the second receiving device, which can be an ostomy pouch or an anal collecting bag. The matter will flow from the second receiving device through the coupling arrangement and into the first receiving device in a flow direction as indicated by the arrow in FIG. 3g.

Furthermore, by using Velcro® patches as described and by further providing the adhesive layers with an adhesive which may be re-used, e.g. where surface may be releasable adhered to each other, a releasable coupling arrangement can be provided allowing the first receiving device and the second receiving device to be releasable connected to each other.

FIG. 4a-4c shows in cross-section the view along the lines IVa-IVa, IVb-IVb and IVc-IVc of the coupling arrangement as shown in FIGS. 3b, 3c and 3g respectively.

FIG. 4a shows the second receiving device as shown above. The arrows 1a and 1b indicate the proximal and distal side respectively of the first fecal receiving device 1 and the arrows 30a and 30b indicate the proximal and distal side respectively of the second fecal receiving device 30.

First and second hinge elements 43, 44 connect the first sealing plate 35 and the second sealing plate 36. Such hinge elements may simply be provided as a thinner area of material.

As can be seen in FIG. 4b the first fecal receiving device 1 and the second fecal receiving device 30 are arranged in a coupling arrangement. This is done by axially aligning the first opening with the second opening and arranging the first receiving device and the second receiving device in a coupling position where the first planar coupling member is placed against the second planar coupling member. The adhesive disposed on the first planar coupling member attaches the two coupling members together.

However, the embodiment shown in the figures is provided with hinge elements between the first sealing plate and the second sealing plate. However, as the hinge elements are thinner than the sealing plates a channel 50 is generated when the first receiving device is connected to the second receiving device as shown in FIG. 4b. Thus, using this embodiment as a coupling assembly would result in leakage through channel 50.

However, a person skilled in the art will understand that the hinges could be made of the same thickness as the sealing plates and thereby avoid creation of the channel.

As can be seen in FIG. 4b, the first end 3 of the first fecal receiving device 1 defines a first plane i-i extending into the first receiving bag and the second end 32 of the second fecal receiving device 30 defines a second plane ii-ii extending into the second receiving bag. Although these planes can be turned in different angles relative to each other the flexibility of the receiving bags enables the first plane and the second plane to be parallel arranged and at least partly aligning the first and second opening. Allowing for such aligning provides a flat coupling arrangement, which is comfortable to use and wear.

As mentioned above, the coupling arrangement will be in a flat configuration where the first end and the second end are empty as shown in FIG. 4b. However, when fecal matter flows through, it will expand the coupling arrangement pushing first adhesive part 7 and first sealing plate 35 in a direction transverse to the first and second plane in a direction opposite the second adhesive part 8 and the second sealing plate 36. By forming either the sealing plates or the adhesive parts (or both), the coupling arrangement may return towards its flat configuration when fecal matter has passed.

The first opening has a larger circumference than the second opening. This allows an easier alignment of the two opening and improves the chance that the second opening is fully encircled by the first opening.

Referring to FIG. 4c, the first receiving device and the second receiving device are folded into coupling position where the first planar coupling member and the second planar coupling member are folded at a first folding axis, which crosses the first and the second opening.

Thus, by folding the first and second planar coupling member the surface of the hinge elements 43, 44 would be exposed and placed in contact with the surface of the first planar coupling member 5 of the first receiving device, more specifically the surface of the hinge would be placed in contact with the first and second peripheral areas 9 and 10 and adhere thereto. Thus, channel 50 is closed off and the risk of leakage reduced.

It can be seen from such folding that the first and second plane are aligned i+ii-i+ii by folding the first coupling member and the second planar coupling member around a folding axis AB-AB transverse to the flow direction across the first and second openings (i.e. perpendicular on the drawing). In particular, it can be seen that the planes are aligned by folding the first adhesive part 7 and the first sealing member 35 relative to the second adhesive part 8 and the second sealing member 36 around the axis AB-AB. This provides an even more flat and flush coupling arrangement, i.e. the two receiving devices extend in the same plane. Furthermore, the coupling arrangement also connects the two fecal receiving devices in a more secure manner. It can be understood that the folding axis AB-AB has a direction perpendicular to FIG. 4c.

Alternatively or additionally, the first planar coupling member 5 can be formed with a higher elasticity than the second planar coupling member, and the second planar coupling member has a higher stiffness than the first planar coupling member. Such a relationship allows the first planar coupling member to be stretched around the second planar coupling member when folded. This provides a leak and odor tight fit reducing the risk of leakage.

During normal use, fecal matter and gasses expand the coupling arrangement. In order to prevent the coupling member from unfolding during such expansion of the coupling arrangement, it may be placed in a secured folded coupling position (also shown in FIGS. 3f and 3g). In a secure coupling position, the first locking strip 11, projecting from the first distal planar part 8, is folded and attached to the first adhesive part 7, and the second locking strip 12, projecting from the second adhesive part 8, is folded and attached to the first proximal planar part 7. Thus, the strips will hold the coupling arrangement in its folded coupling position.

Figure 5B:
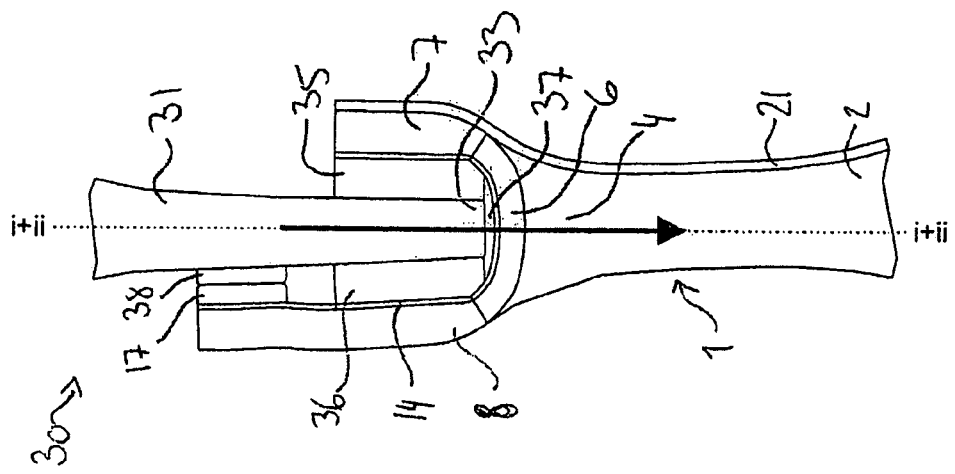
Figure 5A:
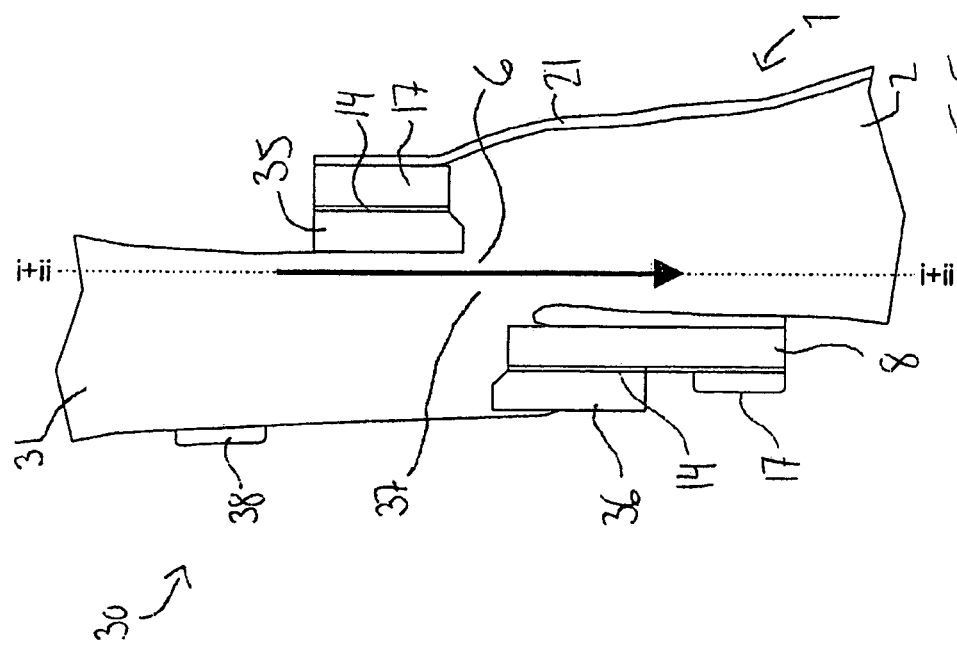

In FIG. 5a, it is shown how the coupling arrangement shown in FIG. 4b expands when fecal matter flows through in the flow direction as indicated by the solid arrow. It can be seen that the flow bends the first adhesive part 7 and the first sealing plate 35 in direction transverse to the flow direction relative to the second adhesive part 8 and the second sealing plate 36 is bent in the opposite direction. Consequently, the first plane i-i and the second plane ii-ii move towards each other to eventually coincide or almost coincide.

As can be seen in FIG. 5b the coupling arrangement shown in FIG. 4c expands in a similar way, although the first and second planes are already coinciding.

The coupling arrangement as shown is suitable for use with the Hide-away® outlet produced by Coloplast A/S as shown. However, as can be understood from the above, coupling arrangements may also be provided together with other types of outlets.

In an alternative embodiment, two sheet materials welded together along their periphery, thereby forming the second compartment, may form the second receiving bag. The second opening may simply be provided by not welding in an area.

Such second opening is aligned with the first opening. Subsequently, the first proximal planar part and the first distal planar part of the first receiving device can be folded around the second receiving bag to provide the coupling arrangement.

In one embodiment, the second end of the bag has an extent equal to or smaller than the extent of the first opening. In such an embodiment, when the first proximal planar part and the first distal planar part are folded the first peripheral area 9 and second peripheral area 10, as shown in the embodiment described with reference to FIG. 1a, will adhere together providing a leak and odor seal.

In one embodiment, a first stiffening element may be provided on the first distal planar part 8 extending from the distal edge to the proximal edge thereof, i.e. from the edge of the first opening and across the first distal planar part. Such stiffening element provides a characteristic difference between the first distal planar part and the rest of the first planar coupling member and allow a controlled folding of the first planar coupling member. Such stiffening element does not necessarily have to be formed of only one part but may comprise several parts.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

Reference Numbers
1. first fecal receiving device
2. first receiving bag
3. first end
4. first opening
5. first planar coupling member
6. first through going hole
7. first proximal planar part, first adhesive part
8. first distal planar part, second adhesive part
9. first peripheral area
10. second peripheral area
11. first locking strip
12. second locking strip
13. release liner
14. adhesive layer
15. first Velcro® hooks patch
16. second Velcro® hooks patch
17. third Velcro® hooks patch
19. first Velcro® loop patch
20. second Velcro® loop patch
21. biasing element
30. second receiving device
31. second receiving bag
32. second end
33. second opening
34. second planar coupling member
35. second distal planar part, first sealing plate
35. second proximal planar part, second sealing plate
37. second through going elongated opening
38. second Velcro® loop patch
39. third locking strip
40. fourth locking strip
41. fourth Velcro® hook patch
42. fifth Velcro® hook patch
43. first hinge element
44. second hinge element
50. channel

What is claimed is:

1. A coupling arrangement for fecal management connecting a first fecal receiving device to a second fecal receiving device in a fluid tight manner while allowing flow in a flow direction from the first fecal receiving device to the second fecal receiving device or vice versa, said coupling arrangement comprising:
   a first opening provided in a first end of a first bag of the first fecal receiving device and a second opening provided in a second end of a second bag of the second fecal receiving device;
   a first plane and a second plane defined by the first end and the second end respectively;
   a first planar coupling member arranged at least partly around the first opening; and
   a second planar coupling member arranged at least partly around the second opening,
   a first proximal surface of the first planar coupling member being placed against a second proximal surface of the second planar coupling member, and the first planar coupling member being attached to the second planar coupling member enabling the first plane and the second plane to be parallel arranged and at least partly aligning the first and second opening, and
   the first plane and the second plane being aligned by folding the first planar coupling member and the second planar coupling member around a folding axis transverse to the flow direction and across the first opening and the second opening.

2. The coupling arrangement according to claim 1, wherein the first opening and the second opening are formed as elongated openings extending transverse to the flow direction.

3. The coupling arrangement according to claim 1, wherein the first opening and the second opening are aligned.

4. The coupling arrangement according to claim 1, wherein a first adhesive layer is at least partly arranged between the first planar coupling member and the second planar coupling member.

5. The coupling arrangement according to claim 1, wherein a first locking strip and a second locking strip extend transverse to the flow direction from the opposite sides of the first planar coupling member.

6. The coupling arrangement according to claim 1, wherein at least one of the first planar coupling member and the second planar coupling member is formed of a resilient material.

7. The coupling arrangement according to claim 1, wherein the first planar coupling member has a higher stiffness than the second planar coupling member, and the second planar coupling member has a higher elasticity than the first planar coupling member.

8. The coupling arrangement for fecal management according to claim 1, wherein
   the first planar coupling member is formed with a first through going hole communicating with the first opening, said first through going hole defines a first proximal planar part and a first distal planar part of the first planar coupling member,
   the second planar coupling member is formed with a second through going hole communicating with the second opening, said second through going hole defines a second proximal planar part and a second distal planar part of the second planar coupling member, and
   the first proximal planar part is placed against the second distal planar part and the first distal planar part is placed against the second proximal planar part.

9. The coupling arrangement according to claim 8, wherein the first plane and the second plane are aligned by folding the first proximal planar part and the second distal planar part relative to the first distal planar part and the second proximal planar part around the folding axis transverse to the flow direction.

10. The coupling arrangement according claim 8, wherein a first locking strip and a second locking strip extend transverse to the flow direction from the opposite sides of the first distal planar part.

11. The coupling arrangement according to claim 8, wherein a first stiffening element is provided on the first distal planar part extending from a distal edge to a proximal edge thereof.

12. The coupling arrangement according to claim 11, wherein the first stiffening element is formed of at least two parts.

13. The coupling arrangement according to claim 1, wherein the first opening has a larger circumference than the second opening.

14. A method for connecting a first fecal receiving device and a second fecal receiving device into a coupling arrangement in a fluid tight manner while allowing flow in a flow direction from the first fecal receiving device to the second fecal receiving device or vice versa, said coupling arrangement including a first opening provided in a first end of a first bag of the first fecal receiving device and a second opening provided in a second end of a second bag of the second fecal receiving device, a first plane and a second plane defined by the first end and the second end respectively, a first planar coupling member arranged at least partly around the first opening, and a second planar coupling member arranged at least partly around the second opening, a first proximal surface of the first planar coupling member being placed against a second proximal surface of the second planar coupling member, and the first planar coupling member being attached to the second planar coupling member enabling the first plane and the second plane to be parallel arranged and at least partly aligning the first and second opening, the method comprising:
   axially aligning the first opening with the second opening;
   arranging the first receiving device and the second receiving device in a coupling position in which the first planar coupling member is placed against the second planar coupling member; and
   arranging the first receiving device and the second receiving device in a folded coupling position in which the first planar coupling member and the second planar coupling member are folded at a first folding axis, which crosses the first opening and the second opening.

15. The method according to claim 14, further comprising arranging the first receiving device and the second receiving device into a coupling arrangement in a secured folding coupling position wherein a first locking strip, projecting from the first distal planar part, is folded and attached to the first proximal planar part and a second locking strip, projecting from the first distal planar part, is folded and attached to the first proximal planar part.

* * * * *